US005749902A

United States Patent [19]
Olson et al.

[11] Patent Number: 5,749,902
[45] Date of Patent: May 12, 1998

[54] RECORDED DATA CORRECTION METHOD AND APPARATUS FOR ISOLATED CLOCK SYSTEMS

[75] Inventors: Kenneth F. Olson, Edina; William S. Parker, Maple Grove, both of Minn.

[73] Assignee: SurVivaLink Corporation, Minneapolis, Minn.

[21] Appl. No.: 651,553

[22] Filed: May 22, 1996

[51] Int. Cl.$^6$ .................................................. A61N 1/39
[52] U.S. Cl. .................................... 607/5; 128/903
[58] Field of Search .................................. 607/5, 6, 7, 8, 607/60; 128/696, 903

[56] References Cited

U.S. PATENT DOCUMENTS

| 5,402,884 | 4/1995 | Gilman et al. |
|---|---|---|
| 5,405,361 | 4/1995 | Persson. |
| 5,530,859 | 6/1996 | Tobias, II et al. ............ 395/650 |

OTHER PUBLICATIONS

Publication: Cordinated Universal Time,—Time and Frequency Users Manual, NIST Special Publication 559.
Publication: NIST Time and Frequency Services—Article from the Time and Frequency Division NIST, Boulder, CO.
Publication: What Time is It?—Article reprinted from the Internet, Apr. 1, 1996.
Publication: Evolution of Time Measurement—Article from the Time and Frequency Division NIST, Boulder, CO.

Primary Examiner—Scott M. Getzow
Attorney, Agent, or Firm—Patterson & Keough, P.A.

[57] ABSTRACT

A system for automatically correcting data of recorded times from a plurality isolated clocks is disclosed. In the preferred embodiment a computer implemented software is used to download recorded time data from an automatic external defibrillator (AED). The computer also includes an internal clock synchronized with a 911 emergency call time tracking clock. On the initiation of the download, the computer compares its internal clock with the clock on the AED and calculates a correction or adjustment factor. Recorded event data, representing AED intervention times, are downloaded from the AED's memory bank and the software computes a corrected response time using the calculated adjustment factor. This corrected response time is then stored in the AED.

22 Claims, 3 Drawing Sheets

RECORDED DATA CORRECTION METHOD AND APPARATUS FOR ISOLATED CLOCK SYSTEMS

RELATED APPLICATIONS

The present invention is related to a co-pending application which is also assigned to the assignee of this invention entitled: Synchronization Method and Apparatus for Isolated Clocks, which was filed on May 13, 1996, the disclosure of which is incorporated herein by reference.

FIELD OF THE INVENTION

The present invention relates generally to method and apparatus for correcting recorded time data from multiple independent clock systems. In particular, the present invention is a computer implemented software method and apparatus for correcting the time difference inherent between the system time stored in an internal clock of an automated external defibrillators (AEDs) and the system time associated with a 911 computer.

BACKGROUND OF THE INVENTION

AEDs are used by police officers, paramedics and other first-response emergency medical personnel to resuscitate cardiac arrest patients. As such, AEDs are typically used in responding to a 911 call (or a call to another local emergency number). Upon the receipt of such an emergency call, an emergency medical system (EMS) is usually activated, which then dispatches EMS personnel to the scene. EMS personnel are then responsible for reaching the patient and using the AED to defibrillate the patient. After cardiac stabilization the patient is usually transported to the hospital.

In order to adequately assess the response times and efficiencies of an emergency medical system, it is necessary to track the time between the receipt of the 911 call and the time at which care is first administered to the patient. Typically, the response time is calculated by comparing the time of the 911 call (as recorded on the 911 emergency computer) to the time of the first shock delivery (as recorded on the internal real time clock on the AED). Unfortunately, it is often difficult to accurately measure this time due to inherent problems of comparing times on two independent clocks. This is especially true as the internal clock in an AED may differ with time relative to the 911 clock. As a result, the response times measured through the AED real time clock often included errors of many minutes. The magnitude of this error is extremely significant in light of studies which indicate that the chances for successful resuscitation diminish approximately ten percent per elapsed response minute. Accordingly, it is evident that there is a need for increased accuracy in measuring response times using AEDs.

SUMMARY OF THE INVENTION

The present invention is a method and apparatus for correcting time data recorded for an event by discrete timers. Specifically, the preferred embodiment pertains to data correction in the measurement of response times recorded by the internal clocks of an automated external defibrillator (AED) and a computer with 911 emergency system.

A preferred embodiment of the present invention includes the use of a time correction process using software implemented in a computer structured to download information from the AED. The download software is one of the key aspects of the present invention. Further, the computer with the software may be the actual computer which records the 911 emergency call. In the alternate, the computer may be time synchronized with the 911 emergency call computer internal clock.

In its operation mode the computer implemented software enables downloading information from the AED's internal clock and compares it with the 911 timer. Thereafter, the software executes calculations to compare the difference between the recorded times. The time events downloaded from the AED are corrected and then stored in the AED as the corrected times for the rescue.

The present invention therefore enables corrections in data discrepancies relative to event times recorded by different timers. Although the disclosure hereinbelow relates to the preferred embodiment in which time data from an AED internal clock and an internal clock for emergency medical signals are corrected, the invention is generically applicable to systems in which time data from different timer sources must be recorded and corrected to determine real duration of the recorded events.

DETAILED DESCRIPTION OF THE PREFERRED EMBODIMENTS

Figure 1:
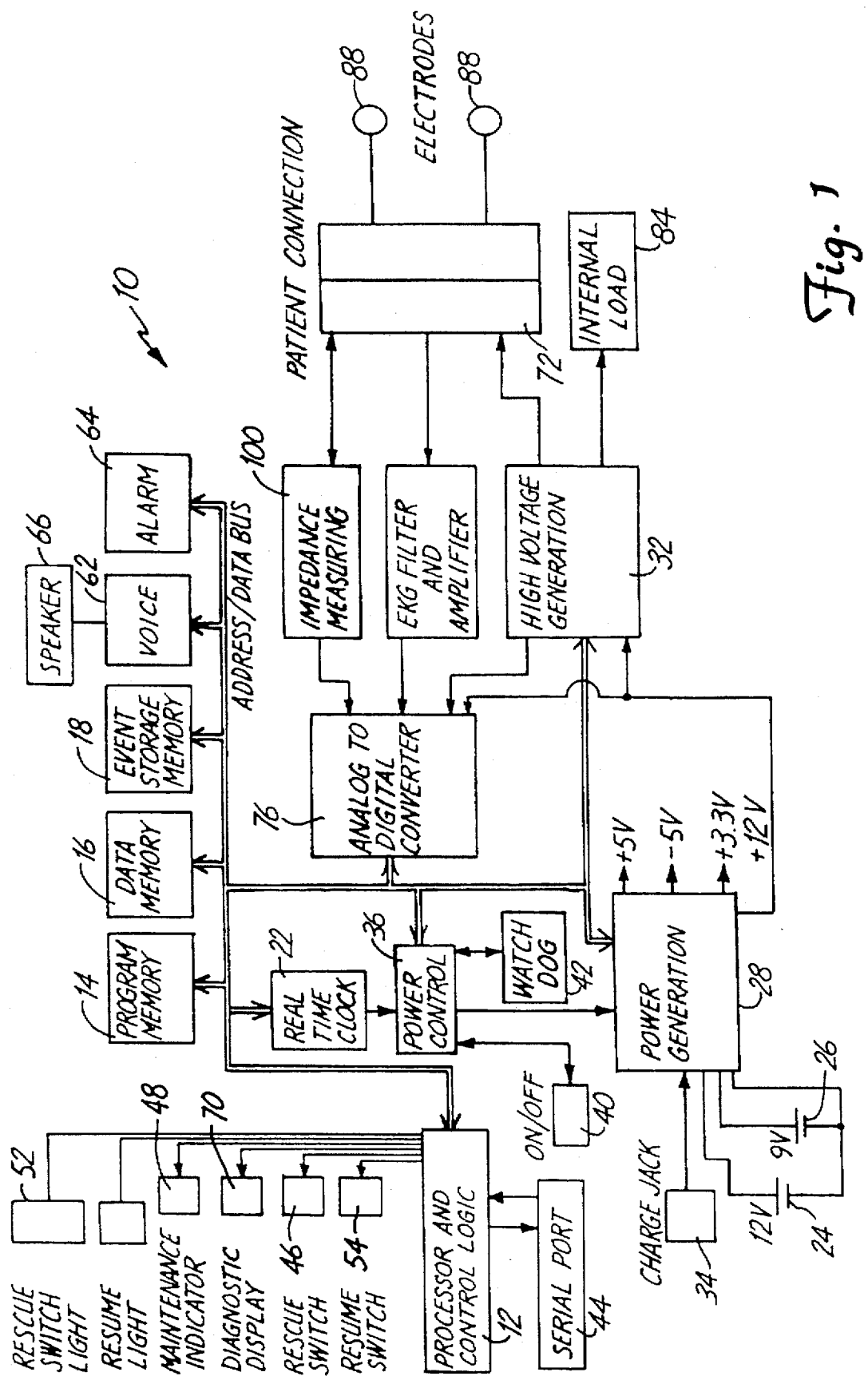
FIG. 1 is a block diagram of the electrical system of an automated external defibrillator (AED).

Referring now to FIG. 1, a block diagram of the electrical system of an automated external defibrillator (AED) is shown. The overall operation of the AED is controlled by a digital microprocessor-based control system 10 which includes a processor 12 interfaced to program memory 14, data memory 16, event memory 18 and real time clock 22. The operating program executed by processor 12 is stored in program memory 14. Data memory 16 is used by processor 12 as a scratch pad memory during the execution of the operating program. Electrical power is provided by a rechargeable twelve volt lead-acid cartridge battery 24 and a nine volt battery 26 which are detachably disposed within the battery compartment and connected to power generation circuit 28. Nine volt battery 26 functions as a back-up battery to power components of the electrical system of the AED during the execution of self-tests and to activate maintenance indicators and alarms (as described below) if the twelve volt battery 24 is low on charge.

A high voltage generation circuit 32 is connected to receive the 12V supply. Charging port at charge jack 34 is coupled to power generation circuit 28, enabling twelve volt battery 24 to be connected to a twelve volt vehicle battery (not shown) or a 120VAC charger (also not shown) and recharged while mounted within the AED.

Power generation circuit 28 is also connected to power control circuit 36 and processor 12. Power control circuit 36 is connected to lid switch 40, watch dog timer 42, real time clock 22 and processor 12. Data communication port 44 is coupled to processor 12 for two-way serial data transfer using an RS-232 protocol. Rescue switch 46 maintenance indicator 48, rescue switch light 52, resume switch 54 and other indicator lights (not shown) of diagnostic display panel 60, voice circuit 62 and piezoelectric audible alarm 64 are also connected to processor 12. Voice circuit 62 is connected to speaker 66. In response to voice prompt control signals from processor 12, circuit 62 and speaker 66 generate audible voice prompts.

High voltage generation circuit 32 is also connected to and controlled by processor 12. Circuits such as 32 are generally known and disclosed, for example, in the commonly assigned Persson, et al., U.S. Pat. No. 5,405,361, which is hereby incorporated by reference. In response to charge control signals provided by the processor 12, high voltage generation circuit 32 is operated in a charge mode during which one set of semiconductor switches (not separately shown) cause a plurality of capacitors (also not shown), to be charged in parallel to the 12V potential supplied by power generation circuit 28. Once charged, and in response to discharge control signals provided by processor 12, high voltage generation circuit 32 is operated in a discharge mode during which the capacitors are discharged in series by another set of semiconductor switches (not separately shown) to produce the high voltage defibrillation pulses. The defibrillation pulses are applied to the patient through electrode connector 72 which is connected to the high voltage generation circuit 32.

The AED electrical system also includes electrocardiogram (EKG) filter and amplifier 74 which is connected between electrode connector 72 and A/D converter 76. The EKG or cardiac rhythm of the patient is processed by filter and amplifier 74 in a conventional manner, and digitized by A/D converter 76 before being coupled to processor 12.

A periodic self-test is initiated and performed by processor 12 at a predetermined time each day (i.e., every twenty-four hours). During the periodic self-test processor 12 performs all the component check operations. In addition to illuminating the appropriate lights on diagnostic display panel 70, processor 12 switches maintenance indicator 48 to its maintenance required state and activates alarm 64 if faults are identified during the daily self-test.

Data representative of the operation of the AED and the monitored cardiac rhythm of the patient are stored in event memory 18 during rescue mode operation. Stored data representative of the operation of AED includes the real time of the occurrence of each of the following events: 1) the placement of electrodes 88 on the patient; 2) the initiation of the cardiac rhythm analysis voice prompt; 3) the initiation of the charging voice prompt; 4) the completion of the charge mode operation of high voltage generation circuit 32; and 5) the actuation of rescue switch 46. The actual time base of the patient's cardiac rhythm is also stored in memory 18.

Figure 2:
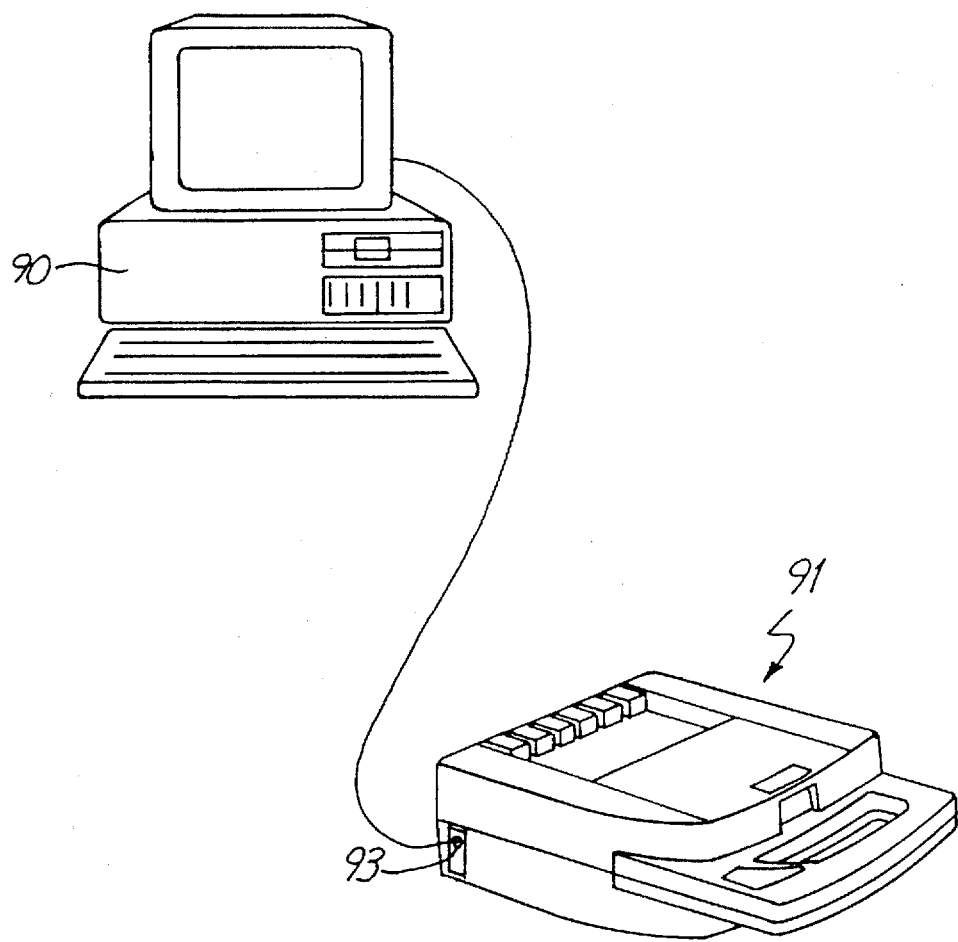
FIG. 2 is a block diagram of the data download system from the AED.

Referring now to FIG. 2, an AED is illustrated generally at 91, having a data communications port 93. Control system 10, which is illustrated in FIG. 1 and which is described in detail above, is housed inside of AED 91. Data stored in event memory 18 of control system 10 can be downloaded through data communications port 93 to a personal computer (PC) 90 interfaced to real time clock 22 of the AED. Preferably, a modem (not shown) associated with PC 90 provides data from a 911 computer. In the alternate, the time data from the 911 computer timer may be entered manually into PC 90. As will be discussed hereinbelow, a software program implemented in PC 90 operates to download and perform the necessary calculations to provide corrections to the time data downloaded from the AED and the 911 computer.

Figure 3:
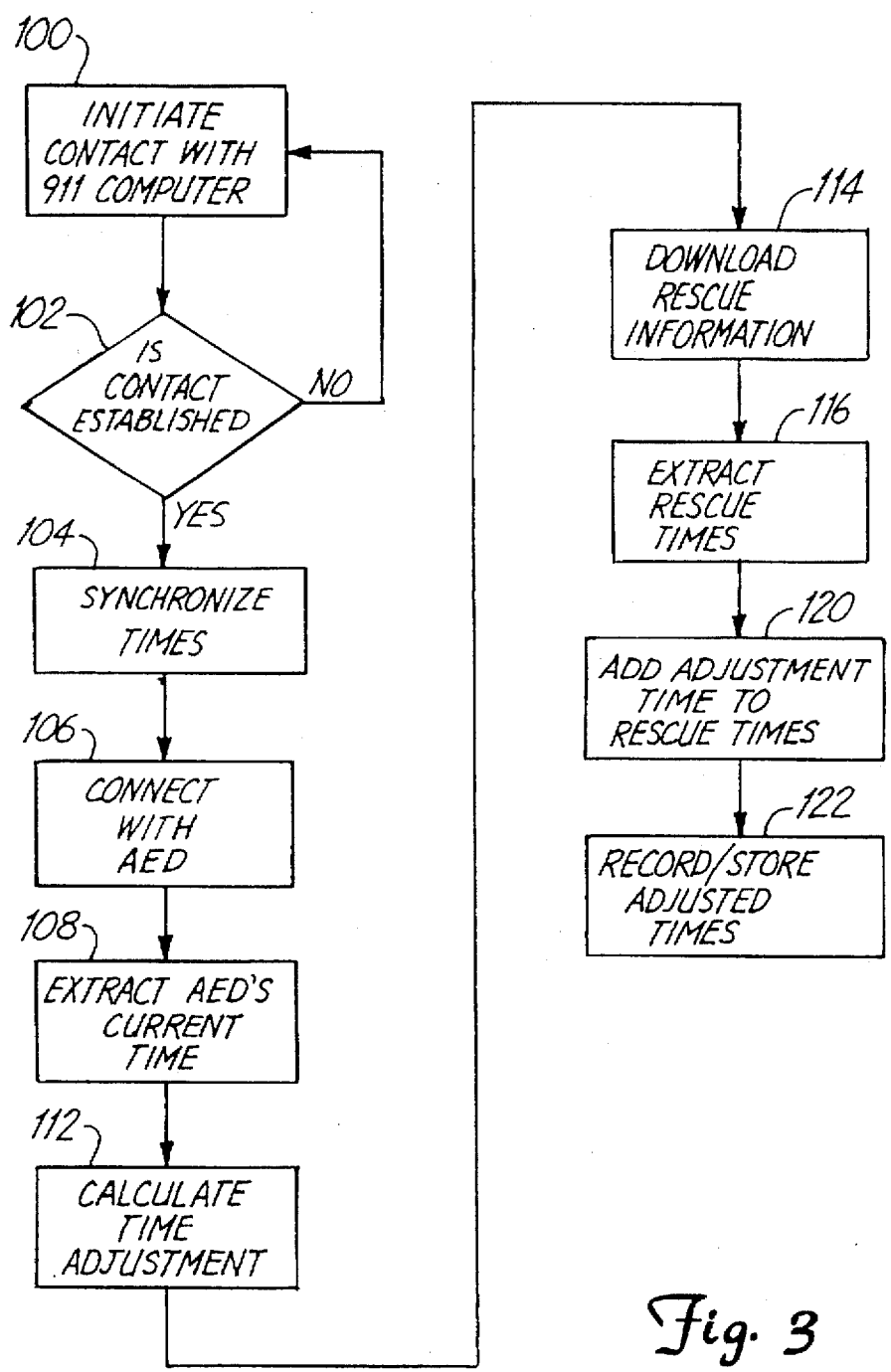
FIG. 3 is a flow chart of the software program implemented in a computer to download data.

FIG. 3 is a flow chart depicting the principal software logic. The program is initiated under block 100 where a modem or other data source is required to provide time data from a 911 computer reporting the time of call of the recorded event. The software logic proceeds to decision block 102 where the establishment of contact with the 911 computer and/or a modem supplying such information is confirmed. The logic stays in this sub-routine loop until positive contact or acquisition of 911 computer time input is identified. The clock on PC 90 and the 911 computer are synchronized under block 104. The software logic then proceeds to connect with the AED real time clock 22 under block 106. Further, the AED's current time is checked and downloaded under block 108. The software calculates time adjustment factors under block 112. Generally, this calculation is made by comparing the relative values of the times received from the AED and the current time on PC 90. Hereinafter, the rescue information stored in event memory 18 of the AED is downloaded under block 114. The software extracts rescue times from among the rescue information under block 116. The program then proceeds to block 120. Under block 120 the program adds adjustment time factors to all time values. Thereafter, the adjusted times are recorded and saved under block 122.

Accordingly, the present invention provides a computer implemented with software which corrects errors arising from time data recorded for an event in which isolated clocks are used.

Although the present invention has been described with reference to preferred embodiments, those skilled in the art will recognize that changes can be made in form and detail without departing from the context and scope of the appended claims.

What is claimed is:

1. A software system implemented in a computer having an internal clock for obtaining time data of events from an AED and a 911 computer, wherein said AED and said 911 computer have time sources having recorded event times with variances, the computer implemented software comprising:

means for communicating with said AED time source and said 911 computer time source;

means for downloading time data from said time sources;

means for assessing values of said time data from said time sources;

means for calculating a time adjustment value to isolate the difference in value between said computer internal clock and said time sources; and means for adjusting said recorded event times from said time sources based on said time adjustment value.

2. The system of claim 1 wherein said time data includes data representative of the operation of said AED and a monitored cardiac rhythm of a patient stored in means for storing events during rescue mode operations.

3. The system of claim 2 wherein said AED includes monitoring means for monitoring the cardiac rhythm of the patient and further includes a control system which includes means for recording data representative of the operation of said AED and the cardiac rhythm of the patient.

4. The system of claim 1 wherein said time data includes time reported via means for carrying time data from said 911 computer reporting the time of call of one of said recorded events.

5. The system of claim 1 wherein said means for downloading further includes means for downloading data representative of the operation of the defibrillator and the cardiac rhythm of the patient.

6. The system of claim 1 wherein the computer with an internal clock includes time storage for storing time information relating to emergency calls recorded by said 911 computer clock, and the computer further includes means for synchronizing the internal clock with the 911 computer clock and means for downloading information from an internal clock of the AED to thereby compare with said 911 computer clock and provide comparative calculations and corrections to the recorded event times.

7. A method for analyzing recorded response times of emergency medical personnel administering care with an automated external defibrillator wherein a computer implemented software device is used to make corrections in the recorded response times, comprising the device-implemented steps of:

storing time information relating to the administration of care in the automated external defibrillator;

calculating the time difference between a clock located on the automated external defibrillator and a clock located on a personal computer;

downloading the administration of care time information from the automated external defibrillator to the personal computer; and adjusting the administration of care time information according to the calculated time difference.

8. The method of claim 7 further comprising the step of storing time information on the computer related to an emergency phone call and comparing the administration of care time information with the emergency phone call time information.

9. The method of claim 8 wherein the step of storing emergency phone call time information includes the steps of storing the emergency phone call time information on an emergency computer and downloading the emergency phone call time information from the emergency computer to the personal computer.

10. The method of claim 9, further comprising the step of establishing a link between the personal computer and the emergency computer and then synchronizing a clock located on the personal computer with a clock on the emergency computer.

11. The method of claim 10, further comprising the steps of manually entering data from the emergency computer and synchronizing said clock on the personal computer with the entered data.

12. The method of claim 7, further comprising the step of storing data representative of the operation of the defibrillator in the defibrillator and downloading the defibrillator operation data to the personal computer.

13. The method of claim 12 wherein said defibrillator operations data is manually entered into the personal computer.

14. The method of claim 7 wherein the step of calculating the time difference between a clock located on the automated external defibrillator and a clock located on a personal computer is further comprised of: i) communicating the current time on the clock of the automated external defibrillator to the personal computer; and ii) comparing the communicated automated external defibrillator clock time with the current time on the clock of the personal computer.

15. A software system implemented in a computer linkable to an AED and a 911 computer to exchange data, wherein said computer has an internal clock for synchronization of recorded events from isolated clocks of said AED and said 911 computer to measure accurate response times by correcting errors arising from time data of said recorded events comprising:

means for storing time data in said computer;

means for storing time data in said AED;

means for storing time of call data in said 911 computer;

means for downloading stored data from said AED and said 911 computer into said computer;

means for calculating variance between data in said computer and said stored data downloaded into said computer; and means for correcting said variance to accurately measure said response times.

16. The software system of claim 15 wherein said means for calculating includes means for comparing relative values of time events down loaded from said AED and current time on said internal clock of the computer.

17. The software system of claim 16 wherein said means for comparing further includes means for extracting rescue times from among rescue information stored in event memory of said AED.

18. The software system of claim 15 wherein said means for correcting includes means for adding adjustment factors to time values.

19. A software system implemented in a computer linkable to an AED and a 911 computer to exchange data and to synchronize event times with said computer, said AED, and said 911 computer, the software system having a set of instructions to analyze recorded response times of emergency medical personnel administering care with said AED wherein said software system makes correction in said recorded response times relative to an internal clock of said computer, a clock in said AED and a clock in said 911 computer the software system comprising:

a process for communicating between said computer and said AED, and between said computer and said 911 computer;

a process for downloading said event times from said AED and said 911 computer;

a process for calculation of event time relationships; and a process for correction and adjustment of said event times.

20. The software system of claim 19 wherein said process for communicating includes a process by which the internal clock of the computer is synchronized with a call time tracking clock in the 911 computer.

21. The software system of claim 20 wherein said process for communicating further includes a data communication process between the AED event memory and the computer to thereby interface a real time clock in said AED with said computer.

22. The software system of claim 19 wherein said process for calculation of event time relationships includes comparing relative values of time received from said AED and the current time on said computer and further includes extracting rescue data among rescue information stored in event memory of said AED.

* * * * *